United States Patent
Howley et al.

(10) Patent No.: US 7,094,412 B2
(45) Date of Patent: Aug. 22, 2006

(54) POXVIRUS CONTAINING FORMULATIONS AND PROCESS FOR PREPARING STABLE POXVIRUS CONTAINING COMPOSITIONS

(75) Inventors: Paul Howley, Glen Waverly (AU); Karl Heller, Unterföhring (DE); Ingmar Räthe, Munich (DE)

(73) Assignee: Bavarian Nordic A/S, Kvistgaard (DK)

( * ) Notice: Subject to any disclaimer, the term of this patent is extended or adjusted under 35 U.S.C. 154(b) by 0 days.

(21) Appl. No.: 10/496,858

(22) PCT Filed: Nov. 28, 2002

(86) PCT No.: PCT/EP02/13434

§ 371 (c)(1), (2), (4) Date: May 26, 2004

(87) PCT Pub. No.: WO03/053463

PCT Pub. Date: Jul. 3, 2003

(65) Prior Publication Data

US 2005/0019349 A1 Jan. 27, 2005

(30) Foreign Application Priority Data

Dec. 10, 2001 (DK) ................ 2001 01831

(51) Int. Cl.
| | |
|---|---|
| *A61K 39/275* | (2006.01) |
| *A61K 39/285* | (2006.01) |
| *C12N 7/00* | (2006.01) |
| *C12N 7/01* | (2006.01) |
| *C12N 7/02* | (2006.01) |

(52) U.S. Cl. ............... 424/232.1; 424/199.1; 435/235.1; 435/239

(58) Field of Classification Search ........... 424/199.1, 424/232.1; 435/235.1, 239
See application file for complete search history.

(56) References Cited

U.S. PATENT DOCUMENTS

| 3,577,526 | A | * | 5/1971 | Valette ............ 424/232.1 |
| 3,915,794 | A | | 10/1975 | Zygraich et al. |
| 4,380,582 | A | * | 4/1983 | Orlando et al. ......... 435/239 |
| 5,185,146 | A | * | 2/1993 | Altenburger ........... 424/199.1 |
| 5,792,643 | A | | 8/1998 | Herrmann et al. |
| 6,258,362 | B1 | | 7/2001 | Loudon et al. |

FOREIGN PATENT DOCUMENTS

| DE | 299 213 | | 4/1992 |
| FR | 7 773 | | 3/1970 |
| WO | WO 98/13500 | * | 4/1998 |
| WO | WO 00/34444 | | 6/2000 |

OTHER PUBLICATIONS

Formulation, Stability and Deliver of Live . . . By Burke et al. (Critical Review—Jan. 1999).

* cited by examiner

*Primary Examiner*—Mary E. Mosher
(74) *Attorney, Agent, or Firm*—Andrew Wilford; Jonathan Myers

(57) ABSTRACT

The present invention relates to a formulation, in particular an aqueous formulation comprising (i) a poxvirus of one of the genera *orthopoxvirus, avipoxvirus, parapoxvirus, capripoxvirus* and *suipoxvirus*, (ii) a disaccharide, (iii) a pharmaceutically acceptable polymer and optionally (iv) a buffer. The aqueous formulation is particularly suitable for freeze drying processes resulting in a stable, freeze-dried, poxvirus containing composition. The invention further concerns a method for preparing a freeze-dried, poxvirus containing composition and the thus obtained product.

20 Claims, 3 Drawing Sheets

Figure 1:
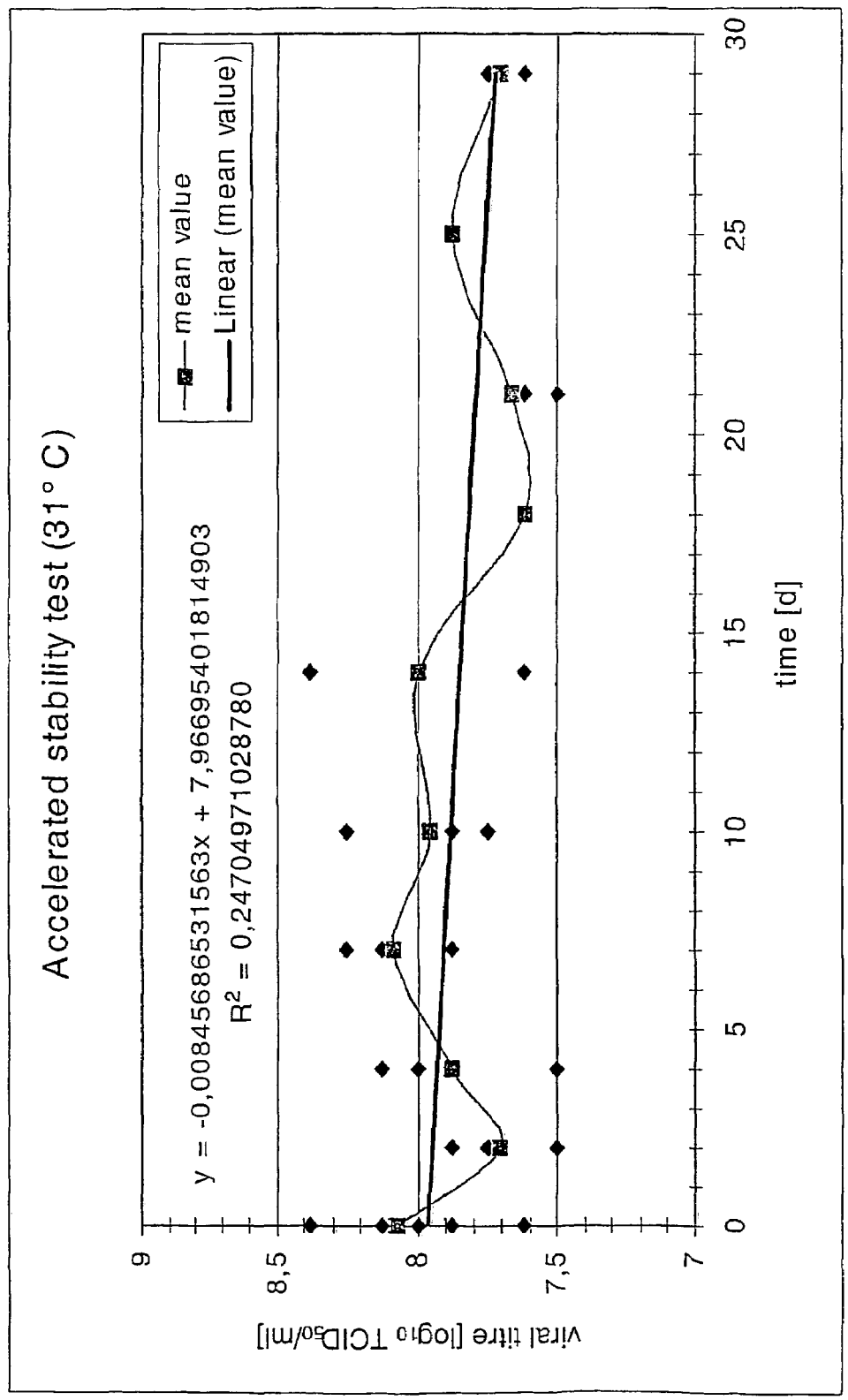

POXVIRUS CONTAINING FORMULATIONS AND PROCESS FOR PREPARING STABLE POXVIRUS CONTAINING COMPOSITIONS

CROSS REFERENCE TO RELATED APPLICATIONS

This application is the US National Phase of PCT/EP02/13434 filed 28 Nov. 2002 and claiming the benefit of the priority of the Danish Patent Application PA2001 01831 filed 10 Dec. 2001.

The present invention relates to a formulation, in particular an aqueous formulation comprising (i) a poxvirus of one of the genera orthopoxvirus, avipoxvirus, parapoxvirus, capripoxvirus and suipoxvirus, (ii) a disaccharide, (iii) a pharmaceutically acceptable polymer and optionally (iv) a buffer. The aqueous formulation is particularly suitable for freeze-drying processes resulting in a stable, freeze-dried, poxvirus containing composition. The invention further concerns a method for preparing a freeze-dried, poxvirus containing composition and the thus obtained product.

BACKGROUND OF THE INVENTION

The poxviridae comprise a large family of complex DNA viruses that replicate in the cytoplasm of vertebrate and invertebrate cells. In humans smallpox was by far the most important poxvirus infection. The causative agent of smallpox is the variola virus, a member of the genus *Orthopoxvirus*. *Vaccinia* virus, also a member of the genus *Orthopoxvirus* in the family of Poxviridae, was used as live vaccine to immunize against smallpox. Successful worldwide vaccination with *Vaccinia* virus culminated in the eradication of *variola* virus (The global eradication of smallpox. Final report of the global commission for the certification of smallpox eradication; History of Public Health, No.4, Geneva: World Health Organization, 1980). In the meantime, most of the stocks of infectious *variola* viruses have been destroyed. However, it can not be excluded that poxviruses inducing smallpox or smallpoxlike diseases might again become a major health problem. Thus, it is necessary to be in a position to produce stable vaccines against poxvirus infections, in particular variola infections, such as vaccines based on *vaccinia* virus.

In the past *vaccinia* viruses have also been used to engineer viral vectors for recombinant gene expression and for the potential use as recombinant live vaccines (Mackett, M., Smith, G. L. and Moss, B. [1982] P.N.A.S. USA 79, 7415–7419; Smith, G. L., Mackett, M. and Moss, B. [1984] Biotechnology and Genetic Engineering Reviews 2, 383–407). This entails inter alia DNA sequences (genes), which code for foreign antigens being introduced into the genome of the *Vaccinia* viruses with the aid of DNA recombination techniques. If the gene is integrated at a site in the viral DNA which is non-essential for the life cycle of the virus, it is possible for the newly produced recombinant *Vaccinia* virus to be infectious, i.e. the virus is able to infect foreign cells and thus to express the integrated DNA sequence (EP 83286 and EP 110385). The recombinant *Vaccinia* viruses prepared in this way can be used, on the one hand, as live vaccines for the prophylaxis of infectious diseases and on the other hand, for the preparation of heterologous proteins in eukaryotic cells. Other examples for recombinant *vaccinia* viruses are viruses harboring therapeutic genes such as suicide genes, ribozyme genes or antisense genes.

Modified *Vaccinia* virus Ankara (MVA) is known to be exceptionally safe. MVA has been generated by long-term serial passages of the Ankara strain of *Vaccinia* virus (CVA) on chicken embryo fibroblasts (for review see Mayr, A., Hochstein-Mintzel, V. and Stickl, H. [1975] Infection 3, 6–14; Swiss Patent No. 568, 392). Examples for MVA virus strains deposited in compliance with the requirements of the Budapest Treaty are strains MVA 572 deposited at the European Collection of Animal Cell Cultures (ECACC), Salisbury (UK) with the deposition number ECACC V94012707, MVA 575 deposited under ECACC V00120707 and MVA-BN with the deposition number ECACC V00083008.

MVA is distinguished by its great attenuation that is to say by diminished virulence or infectiosity while maintaining good immunogenicity. The MVA virus has been analyzed to determine alterations in the genome relative to the wild type CVA strain. Six major deletions of genomic DNA (deletion I, II, III, IV, V, and VI) totaling 31,000 base pairs have been identified (Meyer, H., Sutter, G. and Mayr A. [1991] J. Gen. Virol. 72, 1031–1038). The resulting MVA virus became severely host cell restricted to avian cells. Furthermore, MVA is characterized by its extreme attenuation. When tested in a variety of animal models, MVA was proven to be avirulent even in immunosuppressed animals. More importantly, the excellent properties of the MVA strain have been demonstrated in extensive clinical trials (Mayr et al., Zbl. Bakt. Hyg. I, Abt. Org. B 167, 375–390 [1987], Stickl et al., Dtsch. med. Wschr. 99, 2386–2392 [1974]). During these studies in over 120,000 humans, including high-risk patients, no side effects were associated with the use of MVA vaccine. Recombinant MVA useful as vaccines have already been constructed (see, e.g., WO 97/02355) and are used in clinical trials. WO 98/13500 discloses a recombinant MVA containing and capable of expressing DNA sequences encoding dengue virus antigens. The foreign DNA sequences were recombined into the viral DNA at the site of a naturally occurring deletion in the MVA genome.

An MVA strain showing an even stronger attenuation and enhanced safety characteristics is the strain MVA-BN, deposited at the European Collection of Animal Cell Cultures (ECACC), Salisbury, UK with the deposition number V00083008.

Besides *vaccinia* virus other poxviruses have been used as vectors to deliver genetic information into mammalian cells. In this context reference is made to avipox viruses such as fowlpoxvirus. Fowlpoxviruses containing HIV genes in the genome are disclosed in U.S. Pat. Nos. 5,736,368 and 6,051,410.

Processes for preparing poxvirus containing compositions suitable as vaccines are known to the person skilled in the art (see for example Joklik W. K., Virology (1962),18, 9–18; Richter, K. H., Abhandlungen aus dem Bundesgesundheitsamt (1970), 9, 53–57). The known purification results in aqueous, poxvirus containing solutions or in poxvirus containing sediments. The poxviruses in these solutions and sediments are not stable, i.e. the infectivity of the viruses rapidly decreases. However, it is necessary that a vaccine can be stored and distributed in a stabilized form, especially when the vaccines need to be transported in tropical regions with limited distribution infrastructure. A freeze-dried product can be stored at temperatures in the range from 4° C. to 25° C. This is a clear advantage compared to the standard storage conditions for liquid formulations, which have to be stored below −20° C. ("Cryopreservation and freeze-drying protocols" Day J, McLellan M; Methods in Molecular Biology, 38, 1995, Humana Press).

Processes for the freeze-drying of poxviruses, in particular *vaccinia* virus, and virus containing compositions and solutions suitable for this purpose are known (Burke et al., Critical Reviews in Therapeutic Drug Carrier Systems (1999), 16, 1–83). In general terms freeze-drying of a vaccine involves freezing of the vaccine containing aqueous formulation suitable for freeze-drying, followed by removing water by sublimation under conditions of reduced pressure and low temperatures and further followed by removal of water by desorption under conditions of reduced pressure and higher temperatures The known poxvirus-containing formulations for freeze-drying have important disadvantages. Many of the known *vaccinia* virus containing compositions for freeze-drying contain peptone or haemaccel, which are often of animal origin. However, there are concerns that animal diseases such as BSE could be transmitted from animal to man via animal products such as peptone, gelatine or haemaccel. Moreover, the poxviruses in the known virus containing formulations for freeze-drying have not been purified. Thus, the poxvirus containing compositions for freeze-drying known in the prior art contain inter alia large amounts of proteins derived from the cells of the cell or tissue culture system and from the bovine serum used during cell cultivation, respectively.

The person skilled in the art also knows freeze-drying compositions that do not contain additional compounds of animal origin (which are e.g. peptone or haemaccel). In this case the compositions contain the following compounds alone or in certain combinations: sodium glutamate, sorbitol, lactose, salts, amino acids and glycerin. However, the product obtained after the freeze-drying process is often rather unstable, i.e. the overall loss in virus titer is unacceptably high during storage. Moreover, it has been shown that the poxvirus tends to form aggregates in some of these formulations and that other compounds precipitate before or during freezing.

U.S. Pat. No. 3,577,526 discloses a smallpox vaccine characterized by the fact that it is made up of a ground virus material of the vaccine dispersed in sucrose. The amount of sucrose is in the range of 20 to 40%. The formulation may further comprise 5% dextran. The term ground virus refers to virus derived from pulps and pustules. Basically, the lymph is ground to break up lumps and separate the liquid from the dead hair and skin. Thus, the protein load of the vaccine preparation is very high and contributes to the stabilization of the virus.

OBJECT OF THE INVENTION

It is an object of the present invention to provide a poxvirus containing formulation, in particular an aqueous poxvirus containing formulation, for freeze-drying which leads to a stable freeze-dried product, wherein the poxvirus is preferably a purified or at least partially purified virus. It is a further object of the present invention to provide an aqueous poxvirus containing formulation in which the poxviruses do not tend to aggregate and in which the components do not precipitate before or during freezing. It is a further object of the present invention to provide poxvirus containing formulation, in particular an aqueous poxvirus containing formulation, comprising low amounts of non-poxvirus associated proteins. It is a further object of the present invention to provide a stable, freeze-dried, poxvirus containing composition and a method for obtaining said composition.

DETAILED DESCRIPTION OF THE INVENTION

The present invention provides poxvirus containing formulation, in particular an aqueous poxvirus containing formulation. The formulation, in particular the aqueous formulation may be suitable for freeze-drying of said poxvirus. Furthermore, the invention provides the freeze-dried, poxvirus containing product. The formulation according to the present invention, in particular the aqueous formulation, comprises the poxvirus, a disaccharide, a pharmaceutically acceptable polymer and optionally further a buffer. Although the freeze-dried formulation according to the present invention neither contains stabilizing additives of animal origin such as peptone, gelatine, haemaccel nor high amounts of proteins derived from the system used to amplify the virus (such as cell culture systems), the virus in the formulation is surprisingly stable, i.e. the poxvirus in the freeze-dried composition remains infectious for long periods of time, even at high storage temperatures such as room temperature or 37° C.

If not specified otherwise the term "room temperature" as used in the present specification corresponds to a temperature of 20 to 25° C.

The poxviruses to be freeze-dried are any poxviruses selected from the group consisting of *Orthopoxviruses, Parapoxviruses, Avipoxviruses, Capripoxviruses* and *Suipoxviruses*. These viruses might be useful as a vaccine for human beings or animals (Virology, $3^{rd}$ edition, 1995, ed.-in-chief: Fields, B. N.). Particularly preferred poxviruses are viruses of the genera *Orthopoxvirus* or *Avipoxvirus*. Preferred examples of poxviruses belonging to the genus avipoxvirus are canarypoxvirus and fowlpoxvirus. Preferred examples belonging to the family Orthopoxvirus are *cowpoxvirus* and *vaccinia* virus.

The poxvirus contained in the formulation according to the present invention can be a naturally occurring poxvirus, an attenuated poxvirus or a recombinant poxvirus.

For vaccination of human beings against smallpox the poxvirus in the formulation is preferably a *vaccinia* virus strain. Examples for *vaccinia* virus strains suitable for this purpose are the strains Temple of Heaven, Copenhagen, Paris, Budapest, Dairen, Gam, MRIVP, Per, Tashkent, TBK, Tom, Bern, Patwadangar, BIEM, B-15, Lister, EM-63, New York City Board of Health, *Elstree, Ikeda* and WR. The most preferred *vaccinia* virus strains are modified *vaccinia* virus strain *Ankara* (MVA) and its derivatives, in particular the strain that has been deposited at ECACC with the deposition number V00083008 and strain *Elstree*.

The poxvirus in the formulation according to the present invention is preferably a poxvirus that is essentially a pathogen in the animal or subject to be vaccinated. For this purpose it is preferred either to use attenuated virus strains or to use a poxvirus that naturally replicates in a host species different from the species to be vaccinated and that is not pathogenic in the heterologous host.

An "attenuated virus" is a virus originating from a pathogenic virus but that upon infection of the host organism leads to a lower mortality and/or morbidity compared to the non-attenuated parent virus. Examples of attenuated poxviruses are known to the person skilled in the art. Most preferred is modified *vaccinia* virus *Ankara* (MVA). Typical MVA strains are MVA 575 and MVA 572 that have been deposited at the European Collection of Animal Cell Cultures under the deposition numbers ECACC V00120707 and ECACC V 94012707, respectively. Most preferred is MVA-BN or a derivative thereof, which has been described in WO 02/42480 (PCT/EP01/13628). The content of this application is included in the present application by reference. MVABN has been deposited at the European Collection of Animal Cell Cultures with the deposition number ECACC V00083008.

Examples of poxviruses for which human beings are heterologous hosts and which are not pathogenic in human beings are fowlpoxvirus or canarypoxvirus.

The term "recombinant virus" refers to any virus having inserted into the viral genome a heterologous gene that is not naturally part of the viral genome. A heterologous gene can be a therapeutic gene, a gene coding for a peptide comprising at least one epitope to induce an immune response, an antisense expression cassette or a ribozyme gene. Methods to construct recombinant viruses are known to a person skilled in the art. The most preferred poxvirus vector is MVA, in particular MVA 575 and MVA-BN (see above)

It is known to the person skilled in the art how poxviruses can be amplified and recovered from infected cell cultures. Generally, in a first step eukaryotic cells are infected with the poxvirus that is intended to be part of the formulation according to the present invention. The eukaryotic cells are cells that are susceptible to infection with the respective poxvirus and allow replication and production of infectious virus. Such cells are known to the person skilled in the art for all poxviruses. For MVA an example for this type of cells are chicken embryo fibroblasts (CEF) (Drexler I. et al., J. Gen. Virol. (1998), 79, 347–352). CEF cells can be cultivated under conditions known to the person skilled in the art. Preferably the CEF cells are cultivated in serum-free medium. The incubation time preferably is 48 to 96 hours at 37° C.±2° C. For the infection poxviruses are used at a multiplicity of infection (MOI) of 0.05 to 1 $TCID_{50}$ (TCID=tissue culture infectious dose) and the incubation takes place 48 to 72 hours at the same temperature.

Progress of infection can be observed by looking at cytopathic effects (CPE), typically a significant rounding of the infected cells.

Poxviruses are known to exist in two different forms: poxvirus attached to cellular membranes in the cytoplasm of the infected cells (intracellular mature virions (IMV)) and viruses that have been externalized (extracellular enveloped virions (EEV)) (Vanderplasschen A. et al., J. Gen. Virol. (1998), 79, 877–887). Both viral forms can be used in the formulations according to the present invention. The EEVs can simply be obtained from the supernatant by centrifugation and may be directly suspended in an aqueous formulation including a disaccharide and a pharmaceutically acceptable polymer. However, the virus-containing fractions may comprise cellular detritus and other contaminants. Especially for vaccination of human beings it is thus preferred that the virus is further purified before it is included into a formulation according to the present invention. Methods for the purification of poxviruses are known to the person skilled in the art. The purification step can be e.g. batch centrifugation (e.g. using sucrose cushions) or continuous-flow ultracentrifugation (sucrose gradients), ultrafiltration (e.g. cross-flow filtration using a membrane with a pore size bigger than 500 kDa, but equal or smaller than 0.1 µm), column chromatography (e.g. ion exchange, hydrophobic interaction, size exclusion or a combination) or a combination of some or all of the above (Masuda N. et al., J Bacteriol (1981) 147, 1095–1104).

In order to obtain IMVs the cells have to be harvested in a first step and disrupted in a second step. If the infected cells are cells that can be cultivated in suspension culture the infected cells can easily be harvested by centrifugation. If the infected cells are more or less intact adherent cells it is possible to harvest the cells, i.e. to remove the cells from the culture vial, before subjecting them to the disruption step. Harvesting methods are known to the person skilled in the art. Useful techniques are mechanic methods (e.g. by using a rubber cell scraper), physical methods (e.g. freezing below −15° C. and thawing the culture vessels above +15° C.) or biochemical methods (treatment with enzymes, e.g. Trypsin, in order to detach the cells from the culture vessel). If enzymes are used for this purpose the incubation time should be controlled, since the enzymes might also damage the virus after prolonged incubation times.

Methods for the disruption of cells are also known to the person skilled in the art. The freezing-thawing method described above already results in a partial disruption of the cells. Other known techniques for the disruption of cells include the use of ultrasound. The ultrasound treatment of cells results id a virus containing homogenate.

For vaccination of animals the poxvirus containing homogenate could be used in the formulations according to the present invention. However, it is again preferred to use poxviruses that have been purified at least partially. As outlined above such purification methods are known to the person skilled in the art.

The poxviruses are contained in the formulation, in particular in the aqueous formulation in a concentration range of $10^4$ to $10^9$ $TCID_{50}$/ml, preferably in a concentration range of e.g. $10^5$ to $5 \times 10^8$ $TCID_{50}$/ml, most preferably in a concentration range of e.g. $10^6$ to $10^8$ $TCID_{50}$/ml. The actual concentration depends on the amount of virus to be administered to the human being or animal, which in turn depends on the type of virus to be administered. For the *vaccinia* virus strain *Elstree* a typical vaccination dose for humans comprises $2.5 \times 10^5$ $TCID_{50}$. For the *vaccinia* virus strain MVA-BN a typical vaccination dose for humans comprises $1 \times 10^8$ $TCID_{50}$.

As pointed out above the poxvirus in the formulation according to the present invention is preferably a purified or at least partially purified virus. The term "purified or at least partially purified virus" refers to the fact that the virus used in the formulation according to the present invention has a purity that is higher than that of the unpurified virus ("ground virus") as used in the vaccines used until the eradication of smallpox (such as disclosed in U.S. Pat. No. 3,577,526). Such a higher purity can be obtained e.g by one or more of the following methods: batch centrifugation (e.g. using sucrose cushions) or continuous-flow ultracentrifugation (sucrose gradients), ultrafiltration (e.g. cross-flow filtration using a membrane with a pore size bigger than 500 kDa, but equal or smaller than 0.1 µm), column chromatography (e.g. ion exchange, hydrophobic interaction, size exclusion or a combination). Particularly preferred is ultrafiltration and/or batch centrifugation by using sucrose cushions. In more general terms the term "purified or at least partially purified virus" refers to virus preparations (such as preparations comprising MVA or *Elstree*) having a titer of at least $10^6$, preferably of at least $10^7$; more preferably of at least $10^8$, even more preferably of at least $5 \times 10^8$ $TCID_{50}$ per mg total protein. For strain *Elstree* typical preparations have a titer of $8 \times 10^8$ $TCID_{50}$ per mg total protein. Methods how to determine the titer of a poxvirus containing preparation are known to the person skilled in the art; one of these methods is outlined in the example section. The total protein content is preferably determined according to the method of Kjeldahl (Lynch, J. M. and Barbano, D. M., Kjeldahl nitrogen analysis as a reference method for protein determination in dairy products. J AOAC Int. 1999 November–December;

82(6):1389–98. Review). It is to be noted that the total protein content is the sum of viral proteins and cellular proteins.

It was unexpected that a formulation comprising a purified or partially purified virus, a disaccharide and a pharmaceutically active polymer is stable, since it was believed that the large amounts of non-virus protein in the unpurified virus preparations contributed to the stability of the prior art formulations.

The formulation according to the present invention, in particular the aqueous formulation, comprises a disaccharide. In contrast to monosaccharides such as glucose which give a good bioprotection during freeze-drying but which have a low collapse temperature and often freeze-dry with collapse, disaccharides have been shown to be effective freeze-drying protectants displaying higher collapse temperatures than monosaccharides.

The disaccharides comprised in the formulations according to the present invention are pharmaceutically acceptable disaccharides having a collapse temperature (Tc) in a range of about −25° C. to −35° C. Typical collapse temperatures are −31° C. for sucrose, −28.5° C. for trehalose and −30.5° C. for lactose. Typical collapse temperatures for the entire formulation according to the present invention are preferably in the range of −50° C. to −20° C. Preferred subranges are e.g. −37° C. to −30° C., −36° C. to −31° C. or −35.7 to −31.2° C.

Preferably the disaccharide is selected from the group consisting of trehalose, lactose and sucrose. Most preferred is sucrose. The disaccharide, preferably sucrose, is contained in the formulation according to the present invention, in particular the aqueous formulation, preferably in a concentration range of 10–100 g/l, more preferably in a range of 20–80 g/l, most preferably in a range of 25–60 g/l. For sucrose a typical concentration is 45 g/l.

The formulation according to the present invention, in particular the aqueous formulation, further comprises a pharmaceutically acceptable polymer. The polymer is preferably selected from the group consisting of dextran and polyvinylpyrrolidon (PVP). The polymer used has to be soluble in the formulation according to the present invention. If dextran is used its molecular weight is preferably in the range of 20,000 to 100,000, more preferably in the range of 30,000 to 70,000, most preferably in the range of 36,000 to 44,000. The most preferred dextran has an average molecular weight of 40,000. The concentration of dextran is in the range of 1 to 50 g/l, preferably in a range of 2 to 40 g/l or 3 to 30 g/l. Particularly good results have been observed in the ranges of 5 to 50 g/l, 5 to 40 g/l or 5 to 30 g/l. Even more preferred is the range of 8 to 30 g/l. The most preferred range is 10 to 27 g/l. An example for a preferred concentration is 18.9 g/l. The preferred concentrations and concentration ranges of Dextran as shown above, in particular the range of 5 to 50 g/l and the corresponding subranges, have the particular advantage that the collapse temperature of the formulation is relatively high, which makes it possible to carry out the process in an industrial scale. If PVP is used its molecular weight is preferably in the range of 50,000 to 400,000, more preferably in a range of 70,000 to 360,000. The concentration of PVP is in the range of 5 to 200 g/l, more preferably in a range of 5 to 100 g/l, most preferably in a range of 10 to 40 g/l.

The formulation according to the present invention, in particular the aqueous formulation, further may comprise a buffer. As pointed out above it was one of the objects of the present invention to provide an aqueous poxvirus containing formulation in which the poxviruses do not aggregate and in which no precipitation occurs upon drying. It has been shown unexpectedly that such undesired effects are correlated with the presence of a buffer containing phosphate in the aqueous formulation. Examples for phosphate containing buffer are PBS (phosphate buffered saline) and phosphate buffer. Consequently, this particular object of the invention is solved by an aqueous formulation for freeze-drying that does not contain a phosphate buffer. Thus, the buffer contained in the formulation according to the present invention is preferably selected from the group consisting of TRIS, TBS, MOPS, HEPES and (bi-)carbonate buffers. The most preferred buffers are TRIS and TBS.

The buffer is used in a concentration that is sufficient to exert the required buffer capacity. For TRIS buffers the preferred concentration range is 1–50 mM; the most preferred concentration is 10 mM. The pH is preferably adjusted to a value that on the one hand is pharmaceutically acceptable for administration in human beings or animals and that on the other hand is not detrimental to the virus. Thus the pH should be in the range of 6.0 to 9.0, more preferably in the range of 7.2 to 7.8. The most preferred pH is 7.4.

The unexpectedly good results by using a phosphate free buffer are obtained irrespectively of whether the virus in the formulation is an unpurified, purified or partially purified virus. Purified or partially purified viruses are preferred.

The formulation according to the present invention, in particular the aqueous formulation may contain salts such as NaCl. Typical concentrations for NaCl are in the range of 10 to 200 mM. An example for a preferred NaCl concentration is 140 mM.

The formulation according to the present invention, in particular the aqueous formulation further may comprise L-glutamic acid salts. The salt is preferably a monopotassium salt or a monosodium salt. The concentration of the L-glutamic acid salt is preferably in a range of 0.05–0.5 g/l, more preferably in a range of 0.1–0.15 g/l.

Some particularly preferred aqueous formulations according to the present application are listed in the following table 1. In all formulations listed in table 1 the buffer is 10 mM TRIS, pH 7.4, 140 mM NaCl.

TABLE 1

| Modified Vaccinia Virus Ankara (MVA) [$TCID_{50}$/ml] | First additive [g/l] | Second additive [g/l] | Third additive [g/l] | Run in table 6 |
|---|---|---|---|---|
| $5 \times 10^8$ | 25 (sucrose) | 10.5 (dextran) | 0.06 (L-glutamic acid) | GT 8 |
| $5 \times 10^8$ | 34.5 (sucrose) | 14.5 (dextran) | 0.083 (L-glutamic acid) | GT 8 |
| $5 \times 10^8$ | 45 (sucrose) | 18.9 (dextran) | 0.108 (L-glutamic acid) | GT 9 |
| $5 \times 10^8$ | 60 (sucrose) | 25.2 (dextran) | 0.144 (L-glutamic acid) | GT 9 |
| $1 \times 10^8$ | 45 (sucrose) | 18.9 (dextran) | 0.108 (L-glutamic acid) | — |
| $1 \times 10^8$ | 45 (sucrose) | 3.78 (dextran) | 0.108 (L-glutamic acid) | — |

The aqueous formulation according to the present invention is suitable for freeze-drying. For administration the freeze-dried product has to be reconstituted with an appropriate solvent. According to one embodiment sterile water is added to the freeze-dried product in order to bring the compounds into solution. Preferably, the amount of added water corresponds more or less to the amount of water that has been eliminated during freeze-drying. Thus, according to this embodiment the composition of the reconstituted product is more or less identical to the initial aqueous formulation. It is therefore within the scope of the present invention that the aqueous formulation according to the present invention is used as a vaccine. According to an alternative embodiment the freeze-dried product may also be reconstituted in any other pharmaceutically acceptable diluent that may be used in appropriate amounts. By way of example the diluent may be water comprising one or more of the compounds selected from phenol, glycerol and buffer. The concentration of phenol in the reconstituted product is e.g. 0.5%. As pointed out above, the buffer is preferably not a phosphate buffer.

In summary, this aspect of the invention concerns inter alia the following particularly preferred embodiments: (I) A formulation, in particular an aqueous formulation, comprising or even consisting of a purified or partially purified poxvirus selected from the group consisting of Orthopoxviruses, Parapoxviruses, Avipoxviruses, Capripoxviruses and Suipoxviruses, a disaccharide, a pharmaceutically acceptable polymer and optionally a buffer, wherein the buffer is preferably not a phosphate buffer. Preferably the polymer is dextran, preferably in the amounts as specified above. (II) A formulation, in particular an aqueous formulation, comprising or even consisting of a poxvirus selected from the group consisting of *Orthopoxviruses, Parapoxviruses, Avipoxviruses, Capripoxviruses* and *Suipoxviruses*, a disaccharide, a pharmaceutically acceptable polymer and a buffer, wherein the buffer is not a phosphate buffer and wherein the poxvirus is preferably a purified or partially purified virus. Preferably the polymer is dextran, preferably in the amounts as specified above. (III) A formulation, in particular an aqueous formulation, comprising or even consisting of a poxvirus selected from the group consisting of *Orthopoxviruses, Parapoxviruses, Avipoxviruses, Capripoxviruses* and *Suipoxviruses*, a disaccharide, a pharmaceutically acceptable polymer and optionally a buffer, wherein polymer is dextran in the amounts as specified above, by way of example preferably in the range of 5 to 40 g/l. Preferably the buffer is not a phosphate buffer. Preferably the poxvirus is a purified or partially purified virus.

The term "consisting" as used in the context of options (I), (II) and (III) above, refers to formulations consisting of the above-mentioned compounds only and to formulations containing in addition one or more salts. Examples of salts that may be added to the formulations (I), (II) and (III) consisting of the above defined compounds are KCl, NaCl, sodium-glutamate. Thus, the term "consisting" in the definition of the above defined formulations (I), (II) and (III) does not exclude the possibility to add one or more salts.

By way of example a specific embodiment of the present invention comprises an aqueous formulation comprising a purified or partially purified poxvirus selected from the group consisting of *Orthopoxviruses, Parapoxviruses, Avipoxviruses, Capripoxviruses* and *Suipoxviruses*, a disaccharide, a pharmaceutically acceptable polymer and a buffer, wherein the disaccharide is sucrose in the above specified amounts, wherein the polymer is dextran in the above specified amount and wherein the buffer is not a phosphate buffer. By way of example another specific embodiment of the present invention comprises an aqueous formulation consisting of a poxvirus selected from the group consisting of *Orthopoxviruses, Parapoxviruses, Avipoxviruses, Capripoxviruses* and *Suipoxviruses*, a disaccharide, a pharmaceutically acceptable polymer and optionally a buffer. The poxvirus is preferably a purified or partially purified poxvirus. Preferred amounts and examples of the disaccharide, the polymer and the buffer are outlined above.

It is within the skills of the practitioner how such formulations, in particular an aqueous formulations containing poxviruses can be administered and which amounts of virus are used for vaccination. As pointed out above the vaccines might be used to induce an immune response against the poxviruses itself, in particular if attenuated or non-pathogenic, non-recombinant poxviruses are used. If the poxviruses are recombinant poxviruses an immune response is additionally raised against the recombinant protein/peptide expressed by the poxvirus vector.

The term "formulation" as used above usually refers to liquid formulations, preferably to aqueous formulations, if not stated otherwise. If the concentrations or concentration ranges are defined in "mM", "g/l" and so on this is an indication that the respective formulation is a liquid or even aqueous formulation. The term "aqueous formulation" relates to those formulations in which the diluent is water. However, the scope of the present invention also covers those dry formulations that can be obtained from a liquid or even aqueous formulation according to the present invention by removal of the liquid, irrespective of the method that is used for said removal. Thus, the invention also covers those dry formulations that are obtained by methods other than freeze-drying.

In particular, the present invention further relates to a method for preparing a stable, poxvirus containing composition characterized in that the formulation according to the present invention, in particular the aqueous formulation is freeze-dried. In the present application the terms "stable, poxvirus-containing composition" and "freeze-dried poxvirus containing composition" are used interchangeably if not stated otherwise. The term "stable, poxvirus containing composition" is used in the present application to define poxvirus-containing compositions in which the overall loss in virus titer at an incubation temperature of 37° C. during 28 days is less than 0.5 logs, preferably less than 0.4 logs. A detailed protocol to determine the virus titer and thus the overall loss in virus titer is given in the example section. However, any other protocol to determine the viral titer can also be used.

Methods of freeze-drying are generally known to the person skilled in the art (Day, J. and McLellan, M., Methods in Molecular Biology, Humana Press, (1995) vol. 38).

A freeze-drying process usually consists of the following steps, which are explained in more detail below:
1. Vaccine preparation;
2. Sample freezing;
3. Primary drying (sublimation);
4. Secondary drying (desorption);
5. Product stoppering and removal;
6. Vaccine storage;
7. Reconstitution.

Vaccine preparation: The production and amplification of poxviruses to be used as vaccines has been explained in detail above. The poxviruses are optionally purified. The formulation according to the present invention is obtained by adding the above defined disaccharides, polymers and, optionally, buffer, L-glutamic acid and optionally further additives to the poxvirus preparation.

Sample Freezing:

Freezing of the sample does immobilize the components in the solution, thereby preventing product foaming when the pressure is reduced. Freezing is a two-step process during which water initially nucleates, followed by growth of ice crystals, resulting in a mixture of ice and solute concentrate. Ice nucleation is encouraged by reducing the temperatures and agitating the cooled suspension. In contrast to nucleation, ice growth is encouraged by increasing temperature, thereby decreasing suspension viscosity. Regardless of the precise freezing pattern, proliferation of ice throughout the medium results in an increase of solute concentration. Biopolymers in solution or suspension are damaged or inactivated by exposure to these increasing concentrations of solute. Rapid cooling minimizes exposure of the bioproduct to the concentrate. Above a critical temperature (the glass transition temperature) the mass viscosity may decrease sufficiently so that the glass softens and distorts. It dries to form a structureless sticky residue within the vial. The temperature of the distortion is termed the collapse temperature. More specifically the collapse temperature is defined as the temperature at which the mobility of the water in the interstitial region of the matrix becomes significant. To avoid the distortion the freezing temperature has to be below the collapse temperature of the aqueous formulation. The collapse temperature can be determined according to methods known by the person skilled in the art, e.g. by differential thermal analysis (Jennings, T. A., "Lyophilization, Introduction and Basic Principles", Interpharm Press, Denver, Colo., US, 1999, ISBN 1-57491-081-7, pages 132–134).

If the temperature is too low, water diffusion from the virus may be inhibited, and injury by intracellular ice might occur. Consequently, the person skilled in the art will empirically test several freezing temperatures which are all below the collapse temperature of the aqueous formulation and he will test which temperature leads to a freeze-dried product having the highest titer of infectious poxviruses.

Primary Drying (Sublimation):

The primary drying is that part of the freeze-drying process that drives the sublimation of the solvent (ice) from the frozen matrix. The primary drying process starts after the freeze-dryer attains the required condenser temperature and chamber pressure. The pressure in the chamber is usually lower than 1 mbar, preferably lower than 0.2 mbar. Typically the pressure is in the range of 0.04 to 0.12 mbar. Throughout this specification these conditions are sometimes referred to as "low pressure".

The shelf temperature is increased such that sublimation of the ice in the product matrix occurs and the product temperature is significantly lower than the collapse temperature of the formulation to ensure a completely frozen matrix throughout the entire primary drying process and to ensure freeze-drying without collapse. The temperature may remain constant during the whole primary drying process. Alternatively the shelf temperature can be increased continuously during the primary drying. However, the temperature of the product has to be below the collapse temperature during the whole primary drying process. At the end of the primary drying the dried product still can contain more than 5% moisture (w/w). In order to obtain a product with a moisture content that will not longer support biological growth or chemical reactions it is necessary to carry out a secondary drying step.

Secondary Drying (Desorption):

During secondary drying water vapor is desorbed from the surface of the cake that is formend during primary drying. This is accomplished by increasing the temperature while the chamber is still at low pressures so that water is desorbed from the cake surface.

The shelf temperatures for the secondary drying are determined by the stability of the product and may be in the range of 0° C. to +30° C. The product temperature is usually in the range of −5° C. to 30° C. More preferred is a temperature in the range of −5° C. to 20° C. The secondary drying can be made in two steps. In a first step the product temperature may be in the range of −5° C. to +15° C., preferably in the range of 0° C. to +10° C., more preferably in the range of 2° C. to +7° C. The second step is made at a higher temperature than the secondary drying in the first step. The temperature may be in the range from 0° C. to 30° C., preferably in the range of +5° C. to +20° C. Also the residual moisture content of the formulation depends on the requirements of the product. Some products need higher, some products lower moisture content to achieve best product stability. The optimal residual moisture content as well as the time to reach this has to be determined empirically.

The secondary drying process is continued until the desired moisture is achieved. Methods to determine the moisture of a product are known to the person skilled in the art. In particular the coulometric Karl-Fischer titration can be used (Jennings, T. A., "Lyophilization, Introduction and Basic Principles", Interpharm Press, Denver, Colo., US, 1999, ISBN 1-57491-081-7, pages 415–418). The residual moisture content is preferably lower than 5%, more preferably in a range of 0.5 to 4%, even more preferably in a range of 1 to 3%.

Product Stoppering and Removal:

All product-containing vials are sealed according to methods known to the person skilled in the art. The vials can be sealed under very low pressure (e.g. 0.04–2.56 mbar) directly in the freeze dryer. It is also possible to seal the vials under more or less normal pressure by using a chemically inert gas such as nitrogen or helium. Typically the vials may be sealed in a nitrogen atmosphere at a pressure of 900 mbar. The vials are closed, preferably by using butyl rubber stoppers. Once the product is stoppered the system can be returned to atmospheric pressure and the shelf can be unloaded. Afterwards, the vials further may be sealed with aluminum caps for long-term storage.

Vaccine Storage:

The freeze-dried product can be stored at room temperature (25° C.) and remains stable for at least 18 weeks, preferably at least 20 weeks more preferably at least 22 weeks at this temperature. "Stable at a certain temperature for a certain period of time" means that the loss of viral titer at this temperature is less than 0.5 logs during this time period. However, if cooling is available it is preferred that the freeze-dried product is stored at lower temperatures such as 4° C. Preferably the product is stored in the dark. If this is not possible it is preferred to use coloured glass for storage or any other vials, which avoid a detrimental exposure to light.

Reconstitution.

For reconstitution of the freeze-dried product an appropriate amount of a solvent is added to the freeze-dried product resulting in a pharmaceutically acceptable formulation allowing the administration to human beings or animals. The solvent is preferably water. Usually the solvent is added to the formulation in an amount that corresponds substantially to the amount of solvent lost during the freeze-drying process.

The invention concerns also the freeze-dried product obtained by the process according to the present invention.

Thus, the freeze-dried product according to the present invention comprises (i) a poxvirus, preferably of the genera orthopoxvirus or avipoxvirus, (ii) a disaccharide, (iii) a pharmaceutically acceptable polymer and optionally (iv) a buffer, wherein the pox virus, the disaccharide, the polymer and the buffer are defined as above.

Typical compositions in the freeze-dried product are shown in the following table 2. In all formulations shown in table 2 the amount of virus is $5\times10^8$ $TCID_{50}$/ml.

TABLE 2

| | | | |
|---|---|---|---|
| Amount of DSG [%] in the aqueous formulation before freeze-drying (DSG: 63 g/l dextran MW 36,000–44,000, 150 g/l sucrose, 0.36 g/l L-glutamic acid monopotassium salt monohydrate) | 20 | 30 | 40 |
| Sucrose [%] in freeze-dried product | 54.7 (36 mg) | 58.7 (54 mg) | 58.4 (72 mg) |
| Dextran [%] in freeze-dried product | 23 (15.12 mg) | 24.7 (22.68 mg) | 24.6 (30.24 mg) |
| L-Glutamic acid Mono-potassium salt Monohydrate [%] in freeze-dried product | 0.13 (0.0864 mg) | 0.14 (0.1296 mg) | 0.14 (0.1728 mg) |
| Mean value freeze dried cake [mg] (at filling of 1.2 ml) | 65.8 | 92 | 123.1 |

The freeze-dried product according to the present invention is used for the preparation of a vaccine. To this end the freeze-dried product is resolved/reconstituted as described above and administered to a human being or an animal according to methods known to the person skilled in the art.

BRIEF DESCRIPTION OF THE FIGURES

FIG. 1 shows the stability of MVA containing freeze-dried formulation at a temperature of 31° C. The tested formulation is GT23 (see example section, and table 6). The virus titer in the aqueous formulation according to the present invention is determined before freeze-drying. Freeze-drying was made as described for GT23 (see examples and table 6). After freeze-drying the formulation was stored at 31° C. At the indicated time points the freeze-dried formulation was reconstituted and the viral titer was again determined.

FIGS. 2 and 3 show the results of the same experiment as described in the legend to FIG. 1 with the exception that the incubation temperature was 37° C. in FIG. 2 and 45° C. in FIG. 3.

EXAMPLES

The following examples will further illustrate the present invention. It will be well understood by a person skilled in the art that the provided example(s) in no way may be interpreted in a way that limits the applicability of the technology provided by the present invention to this example(s).

Example 1

Freeze-drying of Formulations Containing Modified *Vaccinia* Virus Strain *Ankara* (MVA)

In this example formulations according to the present invention containing MVA were freeze-dried under different conditions. The freeze-dried product was stored at different temperatures. The stability of MVA in the preparation was analyzed by determing the titer of MVA after reconstitution of the freeze-dried product and comparing it with the MVA titer before freeze-drying. The influence of different storage times on the viral titer was determined. The protocol for the determination of the titer of a MVA containing formulation is given in example 2.

1. Experimental Settings:

Vaccine Preparation/Formulations

To test the freeze-drying process according to the present invention several MVA preparations were used. For the freeze-drying experiments (rows GT1-4, 6–10 and 13–15 in table 6) modified *vaccinia* virus strain *Ankara* (MVA) was used. The virus was purified by 36%- and 40%-sucrose cushions centrifugation followed by resuspension in 1 mM Tris-buffer at pH 9.

In freeze dryings experiments GT1-4 (table 6) no additives were used. The used buffer system was 10 mM Tris with 140 mM NaCl at pH 7.4. For the freeze dryings starting with number GT6 (table 6) different additives were used without changing the buffer system.

Two different formulations with different additives were chosen. The additives were given to the virus containing solutions by adding a dilution buffer. The composition of the dilution buffers used is shown in the following tables 3 and 4. The addition of dilution buffer 1 (DSG) results in an aqueous formulation according to the present invention. The use of dilution buffer 2 (DGG) results in a formulation used for comparative analysis.

TABLE 3

| Dilution buffer 1 (DSG) | Concentration in stock solution [g/l] |
|---|---|
| Dextran (MW 36000–44000) | 63 |
| Sucrose | 150 |
| L-Glutamic acid Monopotassium salt Monohydrate | 0.36 |

TABLE 4

| Dilution buffer 2 (DGG) | Concentration in stock solution [g/l] |
|---|---|
| Dextran (MW 36000–44000) | 63 |
| Glucose | 150 |
| L-Glutamic acid Monopotassium salt Monohydrate | 0.36 |

These dilution buffers were used at different concentrations in the final formulation. Dilution buffer 1 (DSG) was used at 16.7%, 23%, 30% and 40% (v/v), dilution buffer 2 (DGG) at 20% (v/v). The $TCID_{50}$/ml of the final formulation was adjusted to $5\times10^8$ $TCID_{50}$/ml with a physiological Tris-buffer (10 mM Tris-buffer; 140 mM NaCl; pH 7.4).

Sample Freezing

The samples were frozen inside the freeze-dryer (Christ freeze dryer, Type Alpha 2–4). For the formulation with sucrose (DSG) the comparison of different freezing temperatures (−30° C. to −45° C.) showed that the suspension has to be frozen to −40° C., which is below the collapse temperature of the formulation, to get a perfect cake structure. When frozen inside the freeze dryer, −40° C. were reached within about 3.5 to 4.5 hours (starting at about 20° C.).

Primary Drying For the formulation with sucrose (DSG) a collapse temperature of about −30 to −37° C. was assumed on account of the collapse temperature of sucrose (−31° C.). Therefore, the product temperature was adjusted to values in the range of −37 to −41° C., to ensure a completely frozen matrix. Pressures of 0.04 and 0.12 mbar (−50° C. and −40° C. in the phase diagram of water) were used.

The driving force of sublimation during primary drying is the pressure difference between the product and the condenser of the freeze dryer created by their temperature differential. A law of nature is that as the temperature of water is decreased the pressure over that water also decreases. A specific temperature of water is always associated with a specific pressure. The condenser was set to temperatures in the range of −83° C. to −89° C. The pressure in the chamber and the shelf temperature regulates the product temperature. This indicates that the length of the primary drying cannot be shortened very easily, because the condenser temperature is fixed. For increasing the product temperature, $T_C$ of the formulation is the limiting factor.

Secondary Drying

The temperatures for the secondary drying are determined by the stability of the product. Also the residual moisture content of the formulation depends on the requirements of the product. Some need higher, some lower moisture content to achieve best product stability. The optimal residual moisture content as well as the time to reach this has to be determined empirically. Since secondary drying starts when the product reaches a temperature above 0° C., secondary drying was done in two steps. In the first step shelf temperature was regulated for some hours (in the range of 4 to 7 hours) in that way that the product temperature was above 0° C. (in the range of 4 to 6° C.). In that way all possibly existing ice that remained after primary drying was melted. By using such mild conditions to start the secondary drying damages to product will be minimised. Afterwards, the second step was initiated by increasing the product temperature to values in the range of 18 to 21° C. for 20–30 hours. The time for the second step is strongly dependent on the wanted residual moisture of the freeze-dried product. To obtain different residual moisture contents different times were used. As assay to measure the residual moisture content of the freeze-dried material the coulometric Karl-Fischer titration was (Jennings, T. A., "Lyophilization, Introduction and Basic Principles", Interpharm Press, Denver, Colo., US, 1999, ISBN 1-57491-081-7, pages 415–418).

Product Stoppering and Removal

All products made during the process development were sealed under very low pressure (0.04–2.56 mbar) directly in the freeze dryer. The vials were closed using butyl rubber stoppers. Once the product was stoppered the system was returned to atmospheric pressure and the shelf was unloaded. Afterwards, the vials were sealed with aluminum caps for long-term storage.

Vaccine Storage

An important aspect of the formulation exercise is to produce a vaccine that is shelf-stable. Factors influencing stability include residual moisture content, sealing atmosphere composition, and storage conditions, including temperature, humidity, and light.

The different batches produced during the process development were all stored at 4° C. and at room temperature. Furthermore, a few batches were also stored at 31° C., 37° C. and 45° C.

All samples were stored in the dark.

Reconstitution

The freeze-dried samples were reconstituted with autoclaved Milli-Q water. More specifically the water (1.2 ml) was added to the sample using a syringe. The suspension was mixed by gentle shaking. The reconstitution takes only a few seconds. The virus titer of the reconstituted product was determined and compared to the virus titer before freeze-drying.

Accelerated Stability Test

Figure 2:
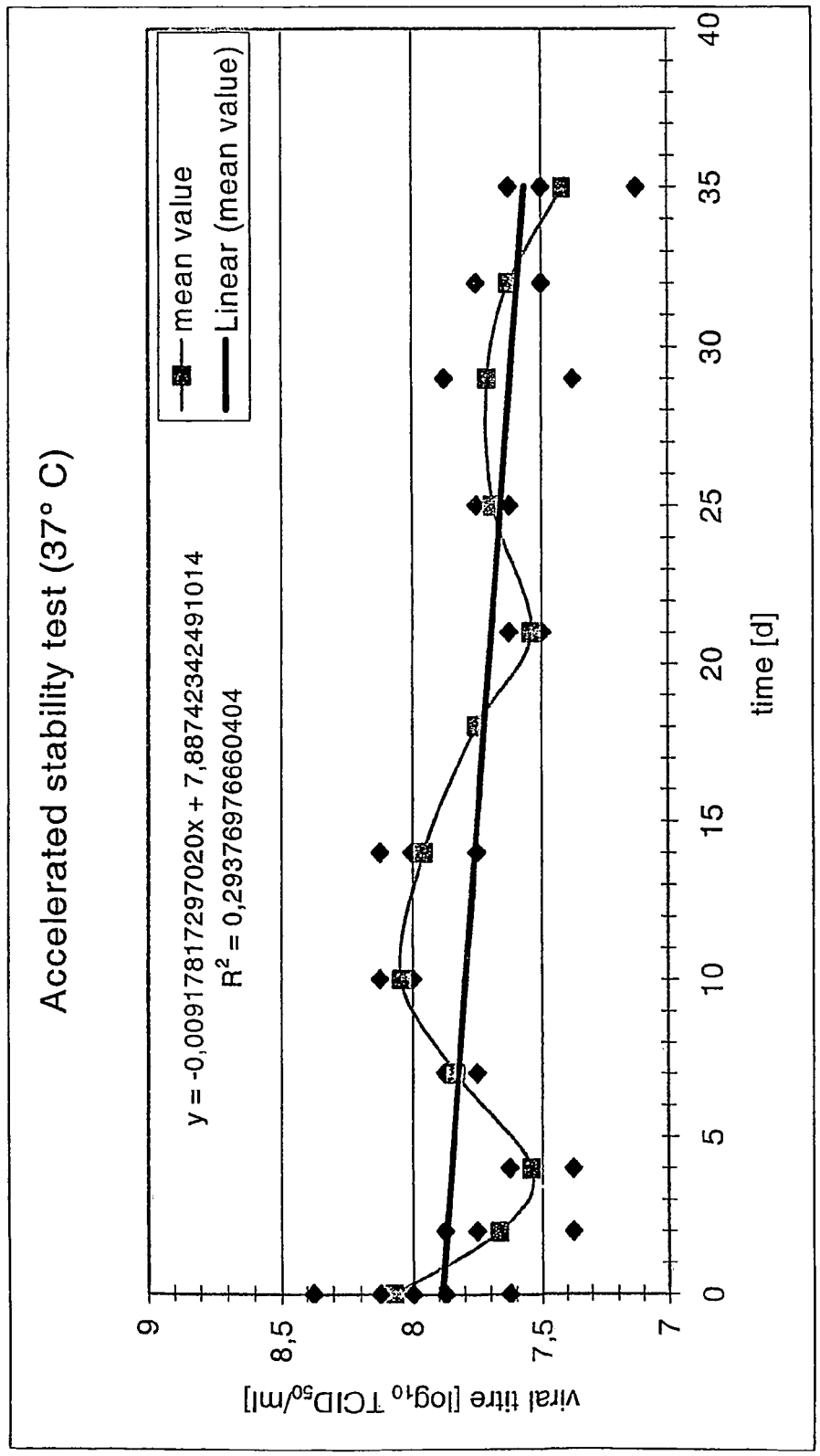
Figure 3:
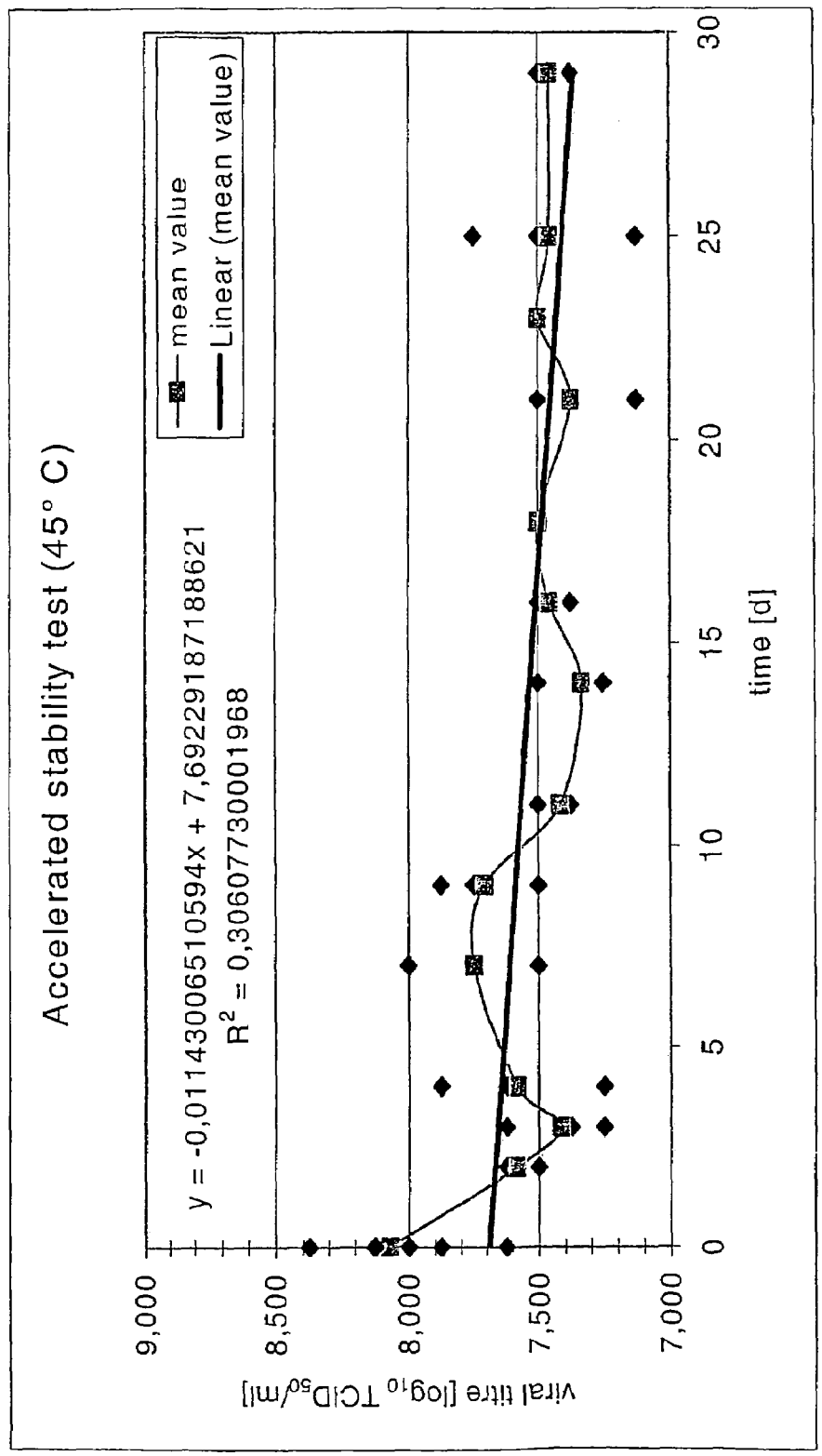

The stability of the formulation GT23 (see table 6) was assessed at 31° C., 37° C. and 45° C. The viral titer was monitored regularly. The results are shown in FIGS. 1 to 3.

2. Results and Conclusion:

MVA was freeze-dried with and without using different additives.

Formulations without additives were shown to be unstable (see table 6). In this context samples were considered as stable when the titer did not drop more than 0.5 log. Thus, the term "stable at a certain temperature for a certain period of time" means that the loss of viral titer at this temperature is less than 0.5 logs during this time period. A formulation "fails" if the loss of virus titer during the indicated time period at the indicated temperature is 0.5 logs or more. Formulations comprising dextran and glucose showed a very low stability at room temperature. The formulations according to the present invention comprising different concentrations of sucrose and dextran proved to be stable. The stability of MVA in the formulations according to the present invention is at least 25 weeks at 4° C. and room temperature.

Detailed information regarding individual experiments is given in table 6:

In table 6 it is shown that the stability of the formulations without additives (table 6, GT1-4) was very poor. After only a few weeks they lost 0.5 logs of their original starting titer, which is not acceptable.

The formulation with 20% (v/v) DGG was not acceptable due to a collapse of the material during the freeze-drying process (data not shown). This collapse is explainable by the low $T_C$ of glucose, which was not markedly increased by the use of dextran, which has a high $T_C$ (−11° C.). For primary drying the lowest possible temperature of the freeze-drying equipment (−45° C.) was used. Therefore, it was not possible to decrease temperatures below the $T_C$ of glucose. The formulations with 30% (v/v) DGG did not collapse. This phenomenon is probably due to the higher overall amount of dextran, which increases. $T_C$ to a value higher than the temperature used for primary drying.

Although the material did not collapse the stability, especially at room temperature, was not satisfying, which might be due to the low solid state $T_C$ of glucose (table 6, GT 10).

Dilution buffer 1 (DSG) was used in most of the experiments. The stabilization with this additive is very good. Due to the high $T_C$ (−31° C.) of sucrose collapse was not a problem with this formulation. The stability of the freeze-dried material was always good (table 6). There were no big differences between the use of 16.7%, 20%, 23%, 28.6%, 30% and 40% (v/v) DSG in the formulation. Stability at 4° C. and room temperature is proven for all 6 formulations. The freeze-dried products with 30% and 40% DSG had a slightly better stability.

One of the formulations (process GT 23, see table 6) was analyzed in detail in an accelerated stability test. The results are shown in FIGS. 1 to 3 and summarized in the following table 5.

TABLE 5

| Temperature [° C.] | Loss of titer (experimental data) | Loss of 0.5 logs after [days] (calculated) |
|---|---|---|
| 31 | 0.245 logs in 29 days | 59 |
| 37 | 0.321 logs in 35 days | 54 |
| 45 | 0.332 logs in 29 days | 44 |

At 31° C. the vaccine has been stored for about 1 month and still met specifications (loss in virus titer is less than half a log). But even at higher temperatures it would be possible to store the vaccine for more than a month, which might be interesting especially for tropical regions.

For the old smallpox vaccines the WHO recommended a method for estimation of stability. If the vaccine lost less than 1 log within 4 weeks at 37° C., it was assumed to be stable for at least one year when stored at 4° C. (acceptance criterion for use of the old vaccine was loss of less than 1 log). As shown the formulation GT23 according to the present invention fulfills this criterion.

Example 2

Titration of Modified *Vaccinia* Virus *Ankara* (MVA)

The titration of Modified *Vaccinia* virus *Ankara* (MVA) is performed in a $TCID_{50}$-based assay using 10-fold dilutions in a 96-well format. At the endpoint of the assay, infected cells are visualised using an anti-vaccinia virus antibody and an appropriate staining solution.

2–3 day old primary CEF (chicken embryo fibroblasts) cells are diluted to $1 \times 10^5$ cells/ml in 7% RPMI. 10 fold dilutions are done with 8 replicates per dilution. Following dilution, 100 µl are seeded per well of 96-well plates. Cells are then incubated over night at 37° C. and 5% $CO_2$.

Dilutions of the virus containing solutions are made in 10-fold steps ($10^{-1}$ to $10^{-12}$ as appropriate) using RPMI without foetal calf serum. Then, 100 µl of every virus sample is added to the cell containing wells. The 96-well-plates are incubated at 37° C. with 5% $CO_2$ for 5 days to allow infection and viral replication.

Cells are stained 5 days after infection with a *vaccinia* virus specific antibody. For the detection of the specific antibody, a horseradish peroxidase (HRP) coupled secondary antibody is used. The MVA specific antibody is an anti-vaccinia virus antibody, rabbit polyclonal, IgG fraction (Quartett, Berlin, Germany #9503-2057). The secondary antibody is anti-rabbit IgG antibody, HRP coupled goat polyclonal (Promega, Mannheim, Germany, #W4011). The colour reaction is carried out according to known techniques.

Every well with cells that are positive in the colour reaction is marked as positive for the calculation of the $TCID_{50}$.

The titre is calculated by using the formula of Spearman [1] and Kaerber [2]. Because all assay parameters are kept constant, the following simplified formula is used:

$$\text{Virus titre }[TCID_{50}/ml] = 10^{[a+1.5+\frac{x_a}{8}+\frac{x_b}{8}+\frac{x_c}{8}]}$$

a=dilution factor of last column, in which all eight wells are positive
$x_a$=number of positive wells in column a+1
$x_b$=number of positive wells in column a+2
$x_c$=number of positive wells in column a+3

TABLE 6

Stability data of poxviruses in different freeze-dried formulations

| Process | Additives | Freezing | Primary drying | Secondary drying | Stability |
|---|---|---|---|---|---|
| GT 1 | — | To −30° C. | Pressure: 0.37 mbar<br>Shelf temperature:<br>2° C. (for 20 h) | Pressure: 0.37 mbar<br>Shelf temperature:<br>5° C. (for 2.5 h)<br>8° C. (for 1 h)<br>10° C. (for 2 h) | Fails after one week at room temperature and 37° C. |
| GT 2 | — | To −40° C. | Pressure: 0.12 mbar<br>product temperature:<br>−13° C. (for 24 h) | Pressure: 2.56 mbar<br>product temperature:<br>−4° C. (for 3.5 h)<br>12° C. (for 4 h) | Fails after 11 days at room temperature and 37° C. |
| GT 3 | — | To −39° C. | Pressure: 0.07 mbar<br>product temperature:<br>−16° C. (for 24 h) | Pressure: 0.07 mbar<br>product temperature:<br>−1° C. (for 2.75 h)<br>7° C. (for 3.5 h) | Fails after 23 days at room temperature |

TABLE 6-continued

Stability data of poxviruses in different freeze-dried formulations

| Process | Additives | Freezing | Primary drying | Secondary drying | Stability |
|---|---|---|---|---|---|
| GT 4 | — | To −45° C. | Pressure: 0.04 mbar product temperature: −37° C. (for 25.5 h) | Pressure: 0.04 mbar product temperature: −3° C. (for 6 h) 14° C. (for 26.5 h) | Fails after 2 weeks at 4° C. and room temperature |
| GT 6 | 30% DSG | To −44° C. | Pressure: 0.04 mbar product temperature: −42° C. (for 23 h) | Pressure: 0.04 mbar product temperature: 5° C. (for 6 h) 16° C. (for 25 h) | Formulation is stable → at 4° C. for at least 34 weeks → at room temperature for at least 20 weeks |
| GT 7 | 23% DSG | To −44° C. | Pressure: 0.04 mbar product temperature: −37° C. (for 22.5 h) | Pressure: 0.04 mbar product temperature: 0° C. (for 7 h) 13° C. (for 24 h) | Formulation is stable for at least 46 weeks at 4° C. and room temperature |
| GT 8 | 16.7% and 23% DSG | To −42° C. | Pressure: 0.04 mbar product temperature: −38° C. (for 24 h) | Pressure: 0.04 mbar product temperature: 4° C. (for 8 h) 17° C. (for 21 h) | at 4° C. and room temperature stable for at least 45 weeks |
| GT 9 | 30% and 40% DSG | To −44° C. | Pressure: 0.04 mbar product temperature: −37° C. (for 25.5 h) | Pressure: 0.04 mbar product temperature: 4° C. (for 6.5 h) 17° C. (for 24 h) | formulation with 30% DSG: stable → at 4° C. for at least 57 weeks → at room temperature for at least 43 weeks formulation with 40% DSG: stable at 4° C. and room temperature for at least 43 weeks |
| GT 10 | 30% DGG | To −35° C. | Pressure: 0.04 mbar product temperature: −37° C. (for 23 h) | Pressure: 0.04 mbar product temperature: 6° C. (for 6.5 h) 19° C. (for 24 h) | Formulation is stable at 4° C. for 42 weeks Formulation fails after 10 weeks at room temperature (RT) |
| GT 11 | 20% DGG | To −45° C. | Pressure: 0.04 mbar product temperature: −41° C. (for 23 h) | Pressure: 0.04 mbar product temperature: 5° C. (for 4 h) 19° C. (for 25.5 h) | Formulations failed at 4° C. after 56 weeks; at RT after 14 weeks |
| GT 12 | 30% DSG | To −40° C. | Pressure: 0.04 mbar product temperature: −37° C. (for 24 h) | Pressure: 0.04 mbar product temperature: 4° C. (for 6 h) 17° C. (for 24 h) | Formulation is stable for at least 54 weeks at 4° C. At 25° C. stable for at least 40 weeks |
| GT 13 | 30% DSG | To −40° C. | Pressure: 0.04 mbar product temperature: −38° C. (for 19 h) −15° C. (for 9 h) | Pressure: 0.04 mbar product temperature: 4° C. (for 15.5 h) 17° C. (for 26.5 h) | Formulation is stable for at least 36 weeks at 4° C. |
| GT 14 | 30% DSG | To −40° C. | Pressure: 0.04 mbar product temperature: −38° C. (for 21.5 h) −13° C. (for 17.5 h) | Pressure: 0.04 mbar product temperature: 15° C. (for 6.5 h) 18° C. (for 26.5 h) | Formulation is stable for at least 50 weeks at 4° C. At 25° C. stable for at least 19 weeks |
| GT 15 | 30% DSG | To −41° C. | Pressure: 0.04 mbar product temperature: −37° C. (for 20 h) | Pressure: 0.04 mbar product temperature: 5° C. (for 3 h) 17° C. (for 24.5 h) | Formulation failed after 49 weeks at 4° C.; At 25° C. stable for at least 18 weeks |
| GT 23 | 30% DSG | To −40° C. | Pressure: 0.12 mbar product temperature: −34° C. (for 21 h) | Pressure: 0.04 mbar product temperature: 7° C. (for 18 h) 17° C. (for 28 h) | Data see → Accelerated stability test in FIG. 1.3 |

INDICATIONS RELATING TO A DEPOSITED MICROORGANISM (PCT Rule 13bis)

| A. The indications made below relate to the microorganism referred to in the description |
|---|
| on page __8__, line __18-20__ |

B. IDENTIFICATION OF DEPOSIT   Further deposits are identified on an additional sheet ☐

Name of depositary institution  ECACC
European Collection of Cell Cultures

Address of depositary institution (including postal code and country)
Centre for Applied Microbiology & Research
Salisbury
Wiltshire SP4 0JG, United Kingdom

| Date of deposit | Accession Number |
|---|---|
| August 30, 2000 | 00083008 |

C. ADDITIONAL INDICATIONS (leave blank if not applicable)   This information is continued on an additional sheet ☐

In respect of all designated States to which such action is possible and to the extent that it is legally permissable under the law of the designated State, it is requested that a sample of the deposited microorganism be made available only by the issue thereof to an independent expert, in accordance with the relevant patent legislation, e.g., EPC Rule 28 (4); UK Patent Rules 1995, Schedule 2, Paragraph 3; Australian Regulation 3.25(3); Danish Patents Act Sections 22 and 33(3) and generally similar provisions mutatis mutandis for any other designated State.

D. DESIGNATED STATES FOR WHICH INDICATIONS ARE MADE (if the indications are not for all designated States)

E. SEPARATE FURNISHING OF INDICATIONS (leave blank if not applicable)

The indications listed below will be submitted to the International Bureau later (specify the general nature of the indications e.g., "Accession Number of Deposit")

---

| For receiving Office use only | For International Bureau use only |
|---|---|
| ☒ This sheet was received with the international application | ☐ This sheet was received by the International Bureau on: |
| Authorized officer  Cocky van Amstel | Authorized officer |

Form PCT/RO/134 (July 1992)

INDICATIONS RELATING TO A DEPOSITED MICROORGANISM (PCT Rule 13bis)

| A. The indications made below relate to the microorganism referred to in the description |
|---|
| on page ___8___ , line ___13-15___ . |

| B. IDENTIFICATION OF DEPOSIT | Further deposits are identified on an additional sheet ☐ |
|---|---|
| Name of depositary institution ECACC<br>European Collection of Cell Cultures | |
| Address of depositary institution *(including postal code and country)*<br>Centre for Applied Microbiology & Research<br>Salisbury<br>Wiltshire SP4 OJG, United Kingdom | |

| Date of deposit | Accession Number |
|---|---|
| December 7, 2000 | 00120707 |

| C. ADDITIONAL INDICATIONS *(leave blank if not applicable)*    This information is continued on an additional sheet ☐ |
|---|
| In respect of all designated States to which such action is possible and to the extent that it is legally permissable under the law of the designated State, it is requested that a sample of the deposited microorganism be made available only by the issue thereof to an independent expert, in accordance with the relevant patent legislation, e.g., EPC Rule 28 (4); UK Patent Rules 1995, Schedule 2, Paragraph 3; Australian Regulation 3.25(3); Danish Patents Act Sections 22 and 33(3) and generally similar provisions mutatis mutandis for any other designated State. |

| D. DESIGNATED STATES FOR WHICH INDICATIONS ARE MADE *(if the indications are not for all designated States)* |
|---|
| |

| E. SEPARATE FURNISHING OF INDICATIONS *(leave blank if not applicable)* |
|---|
| The indications listed below will be submitted to the International Bureau later *(specify the general nature of the indications e.g., "Accession Number of Deposit")* |

| For receiving Office use only | For International Bureau use only |
|---|---|
| ☒ This sheet was received with the international application | ☐ This sheet was received by the International Bureau on: |
| Authorized officer Cocky van Amstel | Authorized officer |

Form PCT/RO/134 (July 1992)

INDICATIONS RELATING TO A DEPOSITED MICROORGANISM (PCT Rule 13bis)

A. The indications made below relate to the microorganism referred to in the description on page 8, line 13-15.

B. IDENTIFICATION OF DEPOSIT  Further deposits are identified on an additional sheet ☐

Name of depositary institution: ECACC, CAMR
European Collection of Cell Cultures Address of depositary institution (including postal code and country):
Centre for Applied Microbiology & Research
Porton Down,
Salisbury, SP4 OJG, United Kingdom Date of deposit: January 27, 1994

Accession Number: 94012707

C. ADDITIONAL INDICATIONS (leave blank if not applicable)  This information is continued on an additional sheet ☐

In respect of all designated States to which such action is possible and to the extent that it is legally permissable under the law of the designated State, it is requested that a sample of the deposited microorganism be made available only by the issue thereof to an independent expert, in accordance with the relevant patent legislation, e.g., EPC Rule 28 (4); UK Patent Rules 1995, Schedule 2, Paragraph 3; Australian Regulation 3.25(3); Danish Patents Act Sections 22 and 33(3) and generally similar provisions mutatis mutandis for any other designated State.

D. DESIGNATED STATES FOR WHICH INDICATIONS ARE MADE (if the indications are not for all designated States)

E. SEPARATE FURNISHING OF INDICATIONS (leave blank if not applicable)

The indications listed below will be submitted to the International Bureau later (specify the general nature of the indications e.g., "Accession Number of Deposit")

---

For receiving Office use only
☒ This sheet was received with the international application
Authorized officer: Cody van Amstel For International Bureau use only
☐ This sheet was received by the International Bureau on:
Authorized officer

The invention claimed is:

1. A formulation comprising:
   (a) a purified or partially purified poxvirus selected from the group consisting of *Orthopoxviruses, Parapoxviruses, Avipoxviruses, Capripoxviruses*, and *Suipoxviruses;*
   (b) a disaccharide;
   (c) a pharmaceutically acceptable polymer; and
   (d) a buffer excluding a phosphate buffer,
   wherein the formulation is substantially free of non-poxvirus associated proteins.

2. Formulation according to claim 1 wherein the buffer excluding a phosphate buffer is selected from the group consisting of TRIS, TBS, MOPS, HEPES, and bicarbonate buffers.

3. Formulation according to claim 1 wherein the poxvirus is a *vaccinia* virus.

4. Formulation according to claim 3 wherein the vaccinia virus is selected from the group consisting of strain *Elstree* and modified *vaccinia* virus strain *Ankara* (MVA).

5. Formulation according to claim 1 wherein the poxvirus is a recombinant poxvirus.

6. Formulation according to claim 1 wherein the disaccharide is selected from the group consisting of sucrose, lactose and trehalose.

7. Formulation according to claim 1 wherein the concentration of the disaccharide is in a range of 10 to 100 g per liter.

8. Formulation according to claim 1 wherein the pharmaceutically acceptable polymer is selected from the group consisting of dextran and polyvinylpyrrolidone.

9. Formulation according to claim 8 wherein the dextran has a molecular weight in the range of 30,000 to 70,000 and has a concentration of 1 to 50 g/l.

10. Formulation according to claim 1 further comprising glutamic acid.

11. Formulation according to claim 1 wherein the collapse temperature is in the range of −37° C. to −30° C.

12. Formulation according to claim 1 wherein the poxvirus is an MVA strain or strain *Elstree*, and the disaccharide is sucrose.

13. Formulation according to claim 1 wherein the purified or partially purified poxvirus is a virus having a titer of at least $10^6$ TCID$_{50}$ per mg total protein.

14. A stable poxvirus-containing vaccine which comprises the formulation according to claim 1 in freeze-dried form.

15. The stable poxvirus-containing vaccine defined in claim 14 having a residual moisture content in the range of 1 to 3%.

16. The stable poxvirus-containing vaccine according to claim 14 reconstituted with a pharmaceutically acceptable inert solvent.

17. A method of preparing a freeze-dried, stable poxvirus-containing vaccine which comprises the following steps:
   (i) freezing a formulation comprising:
      (a) a purified or partially purified poxvirus selected from the group consisting of *Orthopoxviruses, Parapoxviruses, Avipoxviruses, Capripoxviruses*, and *Suipoxviruses;*
      (b) a disaccharide;
      (c) a pharmaceutically acceptable polymer; and
      (d) a buffer excluding a phosphate buffer, to obtain a frozen formulation, wherein the formulation is substantially free of non-poxvirus associated proteins;
   (ii) primarily drying the frozen formulation obtained according to step (i) under low pressure and at a product temperature allowing sublimation of the ice in the product matrix, wherein the product temperature is lower than the collapse temperature of the formulation, to obtain a freeze-dried product and
   (iii) secondarily drying the freeze-dried product obtained according to step (ii) at low pressure and at a product temperature in the range of 0 to 30° C. until the residual moisture of the freeze-dried product is lower than 5%.

18. The method of preparing the freeze-dried, stable poxvirus-containing vaccine defined in claim 17 wherein according to step (iii) the residual moisture of the freeze-dried product obtained is in the range of 1 to 3%.

19. A method of reconstituting the freeze-dried, stable poxvirus-containing vaccine defined in claim 17, which comprises the step of dissolving said vaccine in a sufficient amount of a pharmaceutically acceptable inert solvent.

20. A method of vaccinating an animal subject, including a human, in need of said vaccination against a poxviral disease, which comprises the step of administering to said animal subject, an amount of the stable poxvirus-containing vaccine defined in claim 16 effective to provide an immune response against said poxviral disease.

* * * * *